US010123953B2

(12) United States Patent
Ramji et al.

(10) Patent No.: US 10,123,953 B2
(45) Date of Patent: Nov. 13, 2018

(54) REDUCTION OF TOOTH STAINING DERIVED FROM CATIONIC ANTIMICROBIALS

(75) Inventors: Niranjan Ramji, Mason, OH (US); Douglas Craig Scott, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 137 days.

(21) Appl. No.: 13/529,044

(22) Filed: Jun. 21, 2012

(65) Prior Publication Data
US 2013/0344011 A1 Dec. 26, 2013

(51) Int. Cl.
| | |
|---|---|
| A61K 8/49 | (2006.01) |
| A61Q 11/00 | (2006.01) |
| A61K 8/73 | (2006.01) |
| A61P 1/02 | (2006.01) |
| A61P 29/00 | (2006.01) |
| A61K 31/4425 | (2006.01) |
| A61K 31/721 | (2006.01) |
| A61K 8/27 | (2006.01) |
| A61K 8/33 | (2006.01) |
| A61K 8/35 | (2006.01) |
| A61K 8/41 | (2006.01) |
| A61K 8/43 | (2006.01) |
| A61Q 17/00 | (2006.01) |
| A61K 8/19 | (2006.01) |
| A61K 8/55 | (2006.01) |
| A61K 8/86 | (2006.01) |

(52) U.S. Cl.
CPC .................. *A61K 8/27* (2013.01); *A61K 8/19* (2013.01); *A61K 8/33* (2013.01); *A61K 8/35* (2013.01); *A61K 8/416* (2013.01); *A61K 8/43* (2013.01); *A61K 8/4926* (2013.01); *A61K 8/55* (2013.01); *A61K 8/73* (2013.01); *A61K 8/86* (2013.01); *A61Q 11/00* (2013.01); *A61Q 17/005* (2013.01)

(58) Field of Classification Search
CPC ... A61K 8/27; A61K 8/33; A61K 8/35; A61K 8/416; A61K 8/43; A61K 8/86; A61K 8/19; A61K 8/55; A61K 8/73; A61K 8/4926; A61Q 11/00; A61Q 17/005
See application file for complete search history.

(56) References Cited

U.S. PATENT DOCUMENTS

| | | |
|---|---|---|
| 3,070,510 A | 12/1962 | Cooley et al. |
| 3,535,421 A | 10/1970 | Briner et al. |
| 3,538,230 A | 11/1970 | Pader et al. |
| 3,678,154 A | 7/1972 | Widder et al. |
| 3,862,307 A | 1/1975 | Di Giulio |
| 3,937,807 A | 2/1976 | Haefele |
| 3,959,458 A | 5/1976 | Agricola et al. |
| 3,988,433 A | 10/1976 | Benedict |
| 4,022,880 A | 5/1977 | Vinson et al. |
| 4,083,955 A | 4/1978 | Grabenstetter et al. |
| 4,136,163 A | 1/1979 | Watson et al. |
| 4,138,477 A | 2/1979 | Gaffar |
| 4,150,052 A | 4/1979 | Watson et al. |
| 4,153,679 A | 5/1979 | Rowsell et al. |
| 4,157,384 A | 6/1979 | Watson et al. |
| 4,178,459 A | 12/1979 | Watson et al. |
| 4,183,914 A | 1/1980 | Gaffar et al. |
| 4,206,215 A | 6/1980 | Bailey |
| 4,230,688 A | 10/1980 | Rowsell et al. |
| 4,323,551 A | 4/1982 | Parran |
| 4,340,583 A | 7/1982 | Wason |
| 4,459,425 A | 7/1984 | Amano et al. |
| 4,465,661 A * | 8/1984 | Schmolka ........................ 424/49 |
| 4,528,180 A | 7/1985 | Schaeffer |
| 4,627,977 A | 12/1986 | Gaffar et al. |
| 4,749,758 A | 6/1988 | Dursch et al. |
| 4,849,213 A | 7/1989 | Schaeffer |
| 4,877,603 A | 10/1989 | Degenhardt et al. |
| 4,939,284 A | 7/1990 | Degenhardt |
| 4,994,262 A * | 2/1991 | Charbonneau et al. ........ 424/52 |
| 5,004,597 A | 4/1991 | Majeti et al. |
| 5,009,882 A | 4/1991 | Degenhardt et al. |
| 5,011,913 A | 4/1991 | Benedict et al. |

(Continued)

FOREIGN PATENT DOCUMENTS

| | | |
|---|---|---|
| FR | 2727860 | 6/1996 |
| GB | 1290724 A | 9/1972 |
| WO | WO2008057136 | 5/2008 |

OTHER PUBLICATIONS

PCT International Preliminary Report on Patentability, dated Dec. 23, 2014, 7 pages.

*Primary Examiner* — Lezah Roberts
(74) *Attorney, Agent, or Firm* — Parker D. McCrary; James E. Oehlenschlager

(57) ABSTRACT

Disclosed are oral care compositions having reduced tooth staining propensity and comprising in a pharmaceutically acceptable carrier, a cationic antimicrobial agent and an anti-stain agent comprising one or more materials from each of at least two of the following chemical groups:

Group 1. anionic agents,

Group 2. aldehydes, ketones, and other reactive carbonyl compounds and

Group 3. nonionic ethoxylated surfactants.

Examples of cationic antimicrobial agent include quaternary ammonium compounds such as cetylpyridinium chloride, cetyl pyridinium fluoride, tetradecylpyridinium chloride, N-tetradecyl-4-ethyl pyridinium chloride and domiphen bromide; chlorhexidine; and metal ion sources to supply metal ions such as stannous, zinc or copper.

8 Claims, 2 Drawing Sheets

(56) References Cited

U.S. PATENT DOCUMENTS

| | | |
|---|---|---|
| 5,093,170 A | 3/1992 | Degenhardt et al. |
| 5,145,666 A | 9/1992 | Lukacovic et al. |
| 5,180,577 A | 1/1993 | Polefka et al. |
| 5,198,220 A | 3/1993 | Damani |
| 5,213,789 A | 5/1993 | Degenhardt et al. |
| 5,213,790 A | 5/1993 | Lukacovic et al. |
| 5,242,910 A | 9/1993 | Damanj |
| 5,281,410 A | 1/1994 | Lukacovic et al. |
| 5,292,501 A | 3/1994 | Degenhardt et al. |
| 5,534,243 A | 7/1996 | Dixon, Jr. et al. |
| 5,578,293 A | 11/1996 | Prencipe et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,980,776 A | 11/1999 | Zakikhani et al. |
| 6,071,434 A | 6/2000 | Davis et al. |
| 6,740,311 B2 | 5/2004 | White, Jr. et al. |
| 7,414,152 B2 | 8/2008 | Galopin et al. |
| RE44,339 E | 7/2013 | Galopin et al. |
| 2003/0211053 A1* | 11/2003 | Szeles et al. ............ 424/50 |
| 2005/0169852 A1 | 8/2005 | Roberge et al. |
| 2008/0247973 A1* | 10/2008 | Baig et al. ............ 424/57 |
| 2008/0253976 A1 | 10/2008 | Scott et al. |
| 2008/0300314 A1 | 12/2008 | Galopin et al. |
| 2009/0068122 A1* | 3/2009 | Pilch ............ A61K 8/347 424/52 |
| 2010/0086498 A1* | 4/2010 | Haught ............ A61K 8/19 424/49 |

\* cited by examiner

Figure 1. Reaction of Aldehyde With Salivary Proteins by Thioacetal Formation
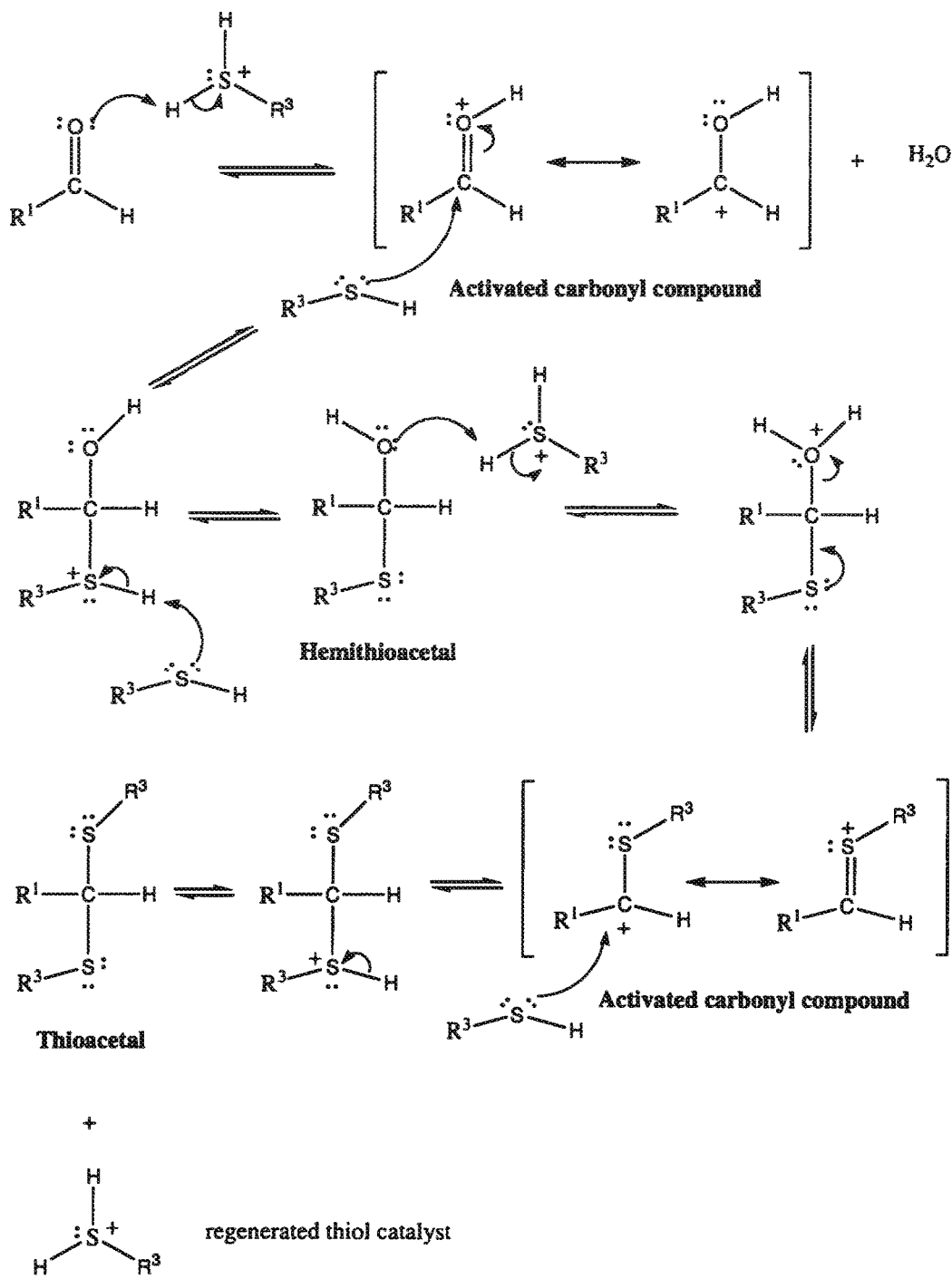
The $R^3$-SH depicted above could be a portion of a salivary protein.

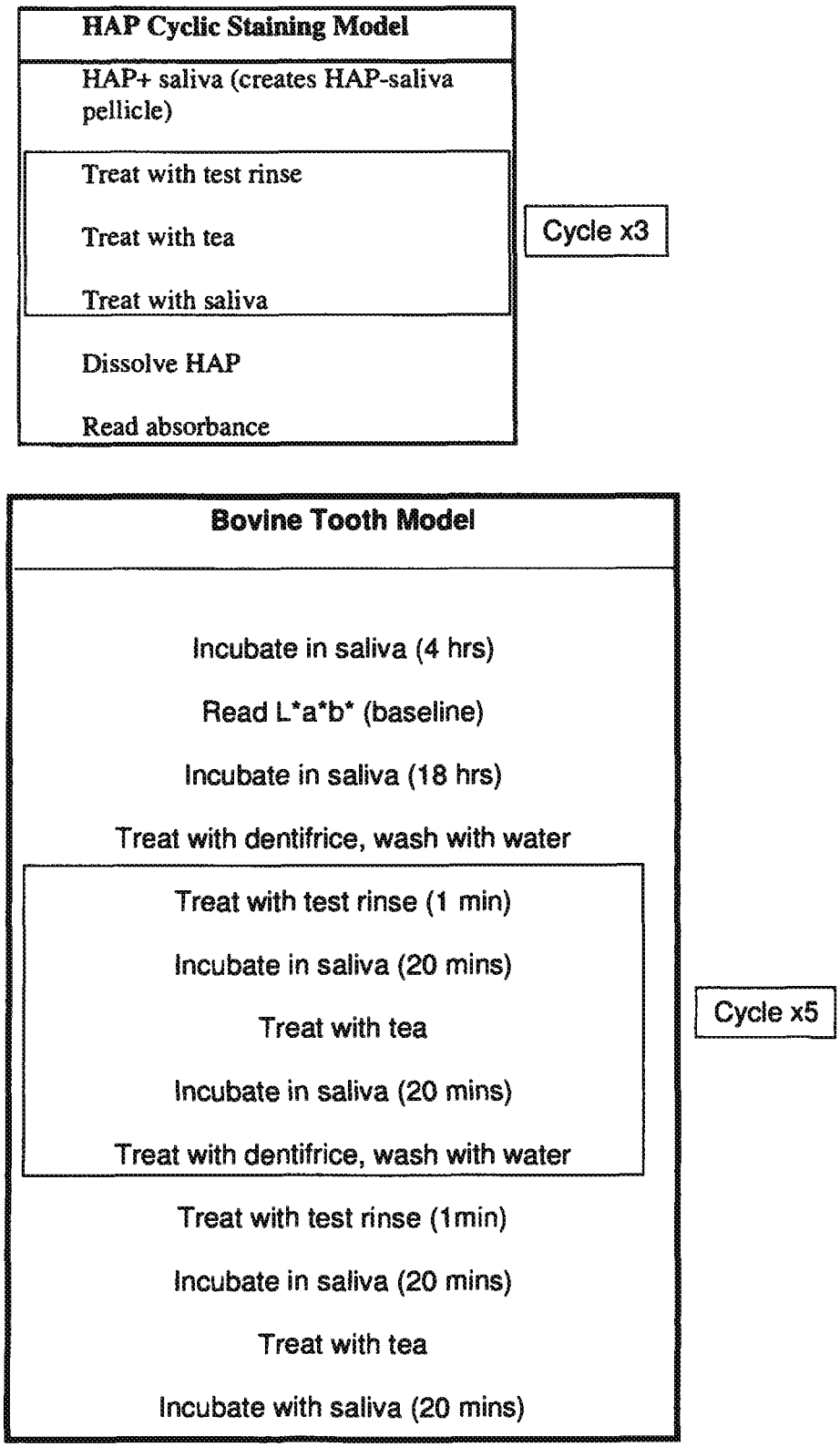
Figure 2. *In Vitro* Staining Models

REDUCTION OF TOOTH STAINING DERIVED FROM CATIONIC ANTIMICROBIALS

TECHNICAL FIELD

The present invention relates to oral care compositions containing an agent to eliminate or reduce tooth staining, specifically staining derived from cationic antimicrobial agents used in oral care compositions to reduce oral bacteria and to prevent and treat bacteria-mediated diseases or conditions of the oral cavity including dental plaque, caries, calculus, gingivitis, periodontal disease and breath malodor.

BACKGROUND OF THE INVENTION

Cationic materials which possess antimicrobial activity have been used in oral compositions to counter oral bacteria and to prevent and treat conditions caused by bacteria in the oral cavity, such as formation of dental plaque and calculus. The formation of dental plaque and calculus and failure to stop their proliferation are the primary cause of dental caries, gingivitis, periodontal disease, and tooth loss. Dental plaque is a mixed matrix of bacteria, epithelial cells, leukocytes, macrophages and other oral exudate. Bacteria comprise approximately three-quarters of the plaque matrix. Any given sample of dental plaque could contain as many as 400 different varieties of microorganisms. This mix includes both aerobic and anaerobic bacteria, fungi, viruses and protozoa. This matrix of organisms and oral exudate continues to expand and coalesces with other plaque growths situated nearby. The bacteria synthesize levans and glucans from sucrose found in the oral cavity providing energy for the microorganisms. These glucans, levans, and microorganisms form an adhesive skeleton for the continued proliferation of plaque. Dental calculus, or tartar as it is sometimes called, is a deposit which forms on the surfaces of the teeth at the gingival margin. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms. Developing plaque can adhere most easily at relatively irregular surfaces, such as those afforded by calculus. Calculus and plaque along with behavioral and environmental factors lead to formation of dental stains, significantly affecting the aesthetic appearance of teeth. Behavioral and environmental factors that contribute to teeth staining propensity include regular use of products that contain staining chemicals or color bodies such as coffee, tea, cola or tobacco and use of stain promoting oral products, such as those containing cationic antimicrobial agents.

Among the most common of cationic antimicrobial agents known to cause tooth staining are quaternary ammonium compounds such as cetylpyridinium chloride and metal ion sources such as stannous fluoride and stannous chloride. The tooth staining potential of these cationic materials has long been documented. Among the many approaches that have been suggested to reduce and control tooth staining and to whiten teeth is by the use of bleaches or oxidants such as peroxide. Essentially, bleaches act by oxidizing color bodies and existing stains. However, bleaches added to oral care products are typically present in low concentrations due to stability and safety limits. At these low concentrations, bleaches such as peroxide, are generally ineffective to control stain and whiten teeth. Furthermore, bleaches do not functionally act to prevent acquisition of stains.

There continues to be a need for oral care products that provide enhanced overall cleaning and hygiene while also controlling tooth staining. Chemical technologies have now been identified that can effectively reduce tooth staining derived from cationic antimicrobials such as CPC. These chemical agents do not involve the use of bleaches or oxidants and significantly do not compromise the bioavailability of the cationic antimicrobials and therefore, their antimicrobial potency.

SUMMARY OF THE INVENTION

The present invention is directed to oral care compositions comprising in a pharmaceutically acceptable carrier, a combination of a cationic antimicrobial agent that causes tooth staining and an anti-stain agent comprising at least two different materials from the following chemical groups:
Group 1. anionic agents,
Group 2. aldehydes, ketones, and other reactive carbonyl compounds and
Group 3. nonionic ethoxylated surfactants.

Examples of Group 1 anionic agents are compounds and polymers containing phosphate, carboxy or sulfate groups such as carboxymethyl dextran (degree of substitution=0.1, MW=10,000) and tetrapotassium pyrophosphate.

Examples of Group 2 aldehydes, ketones and other reactive carbonyl compounds are 4-methoxybenzaldehyde (anisaldehyde); 1,3-benzodioxole-5-carbaldehyde (heliotropin); 3,4-Dimethoxybenzaldehyde (veratraldehyde); 3-methyl-1, 2-cyclopentadione; phenethyl formate, acetophenone; phenylacetaldehyde; 4-methylacetophenone; p-toluacetaldehyde; 3,5,5-trimethyl-2-cyclohexene-1-one (isophorone); gamma-undecalactone; or p-methylcinnamaldehyde.

Examples of Group 3 nonionic ethoxylated surfactants are ethoxylated linear alcohols such as those wherein the number of carbons in the alcohol chain is between about 18 to 55, the ethoxy units by weight is at least 80% and the average molecular weight of the polymer is about 2000 to about 5000.

Examples of cationic antimicrobial agent include quaternary ammonium compounds such as cetylpyridinium chloride, tetradecylpyridinium chloride, N-tetradecyl-4-ethyl pyridinium chloride and domiphen bromide; metal ion sources to supply metal ions such as stannous, zinc and copper; and chlorhexidine.

These and other features, aspects, and advantages of the present invention will become evident to those skilled in the art from the detailed description which follows.

BRIEF DESCRIPTION OF DRAWINGS

FIG. 1 illustrates the reaction between an aldehyde and a salivary protein by thioacetal formation.

FIG. 2 is a summary of the protocols used in the HAP-Pellicle and Bovine Tooth in vitro staining models.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated. All measurements referred to herein are made at about 25° C. unless otherwise specified.

Herein, "comprising" means that other steps and other components which do not affect the end result can be added. This term encompasses the terms "consisting or and "consisting essentially of"."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouth rinse, mousse, foam, denture product, mouthspray, lozenge, chewable tablet or chewing gum. The oral care composition may also be incorporated onto strips or films for direct application or attachment to oral surfaces.

The term "dentifrice", as used herein, means paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having the gel surrounding the paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "mouth rinse", as used herein, includes liquid formulations referred in the art as mouthwashes or dental rinses, mouth sprays, dental solutions and irrigation fluids.

The term "teeth" refers to natural teeth as well as artificial teeth or dental prosthesis.

The terms "pharmaceutically acceptable carrier", "orally acceptable carrier" or "excipients" include safe and effective materials and conventional additives such as those used in oral care compositions including but not limited to fluoride ion sources, antimicrobial agents, anti-inflammatory agents, anti-calculus or anti-tartar agents, desensitizing agents, peroxide sources, abrasives such as silica, buffering agents, alkali metal bicarbonate salts, thickening materials, humectants, water, surfactants, emulsifying agents, anti-stain agents, tooth substantive agents, titanium dioxide, xylitol, essential oils, a coolant, a sweetening agents or other sensates and coloring agents.

The term "essential oils" as used herein refers to volatile oils distilled or expressed from plants and constituents of these volatile oils. Typical essential oils and their main constituents are those obtained for example from thyme (thymol, carvacrol), oregano (carvacrol, terpenes), lemon (limonene, terpinene, phellandrene, pinene, citral), lemongrass (citral, methylheptenone, citronellal, geraniol), orange flower (linalool, β-pinene, limonene), orange (limonene, citral), anise (anethole, safrol), clove (eugenol, eugenyl acetate, caryophyllene), rose (geraniol, citronellol), rosemary (borneol, bornyl esters, camphor), geranium (geraniol, citronellol, linalool), lavender (linalyl acetate, linalool), citronella (geraniol, citronellol, citronellal, camphene), eucalyptus (eucalyptol); peppermint (menthol, menthyl esters), spearmint (carvone, limonene, pinene); wintergreen (methyl salicylate), camphor (safrole, acetaldehyde, camphor), bay (eugenol, myrcene, chavicol), cinnamon (cinnamaldehyde, cinnamyl acetate, eugenol), tea tree (terpinen-4-ol, cineole), and cedar leaf (α-thujone, β-thujone, fenchone). Essential oils are widely used in perfumery and as flavorings, medicine and solvents [See Kirk-Othmer *Encyclopedia of Chemical Technology*, 4$^{th}$ Edition and *The Merck Index*, 13$^{th}$ Edition].

Active and other ingredients useful herein may be categorized or described by their cosmetic and/or therapeutic benefit or their postulated mode of action or function. However, the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed.

In one embodiment of the present invention, oral care compositions are provided comprising a cationic antimicrobial agent comprising one or a mixture of a quaternary ammonium compound selected from cetylpyridinium chloride, tetradecylpyridinium chloride, N-tetradecyl-4-ethyl pyridinium chloride or domiphen bromide; a stannous ion source; a zinc ion source or a copper ion source in combination with an anti-staining agent. The anti-staining agent will preferably comprise one or more materials from each of at least two of the following chemical groups:

Group 1. anionic agents,
Group 2. aldehydes, ketones and reactive carbonyl compounds and
Group 3. nonionic ethoxylated surfactants.

The cationic antimicrobial agents effectively promote oral hygiene, particularly by controlling plaque and calculus proliferation. However, their use has been observed to lead to staining of tooth surfaces or discoloration. The exact mechanisms for the formation of dental stain derived from the use of these cationic antimicrobials have not been clearly established. One explanation that has been offered is that as the cationic antimicrobial agents remove plaque they also denature protein from saliva in the oral environment and the denatured protein can then act as a nucleating agent which is deposited onto and stains or discolors teeth. Another theory is that in the absence of dental plaque, additional $Ca^{+2}$ and $PO_4^{-3}$, particularly from saliva, can be deposited on the tooth surface and such deposits can include color bodies which ultimately stain the tooth surface as a calcified deposit thereon.

Studies were conducted at the Procter & Gamble laboratories to further elucidate the staining problem. Using cetyl pyridinium chloride (CPC) as the stain promoting antimicrobial, it was observed that initial stain formation with CPC occurs on the pellicle surface of the teeth. This stain is a result of the interaction between salivary proteins such as mucin and dietary chromogens or color bodies such as tea polyphenols. The observed stain is exacerbated in the presence of CPC or other cationic antimicrobials such as stannous salts. As has been reported in literature, there are significant interactions between the basic proline rich proteins in saliva and tea polyphenols [See e.g., *J. Dent. Res.*, 84(1), 73-781 (2005); *Biochem. J.*, 297, 249-260 (1994); "Grape and Wine Tannins Precipitation by Proline Rich Proteins", Poster at the 2$^{nd}$ International Electronic Conference of Synthetic Organic Chemistry (ECSOC-2, Sep. 1-30, 1998)]. In fact it has been reported that sodium dodecylsulfate (SDS) polyacrylamide gel electrophoresis of a mixture of saliva and tea extract resulted in the disappearance of the basic proline rich protein bands indicating a precipitation of the basic proline rich proteins with tea polyphenols. The proline rich proteins are inducible in the stomach and saliva and is the body's natural defense mechanism to complex the larger polyphenols to precipitate them, preventing their absorption and hence reducing their toxicity. The interaction of sodium dodecylsulfate (SDS) and nonionic surfactants with mucin has also been reported [*Langmuir*, 18, 9383-9392 (2002)]. Our studies have demonstrated that there is a similar interaction between CPC with other anionic proteins in saliva resulting in the precipitation of the protein and CPC on the tooth surface. The co-precipitate of CPC and protein subsequently interacts with dietary chromogens such as tea polyphenols resulting in tooth staining.

We have found that by the use of certain anionic agents, we are able to reduce aggregation of salivary proteins, either by direct hydrophobic (insertion into non polar region of the protein) or charged interaction of the anionic agent with the salivary proteins or by the formation of a counter ion with the pyridinium ring of the CPC. The anionic agent is more tightly bound to the pyridinium ring than the chloride ion, which then reduces the interaction of CPC with the salivary proteins.

Some aldehydes have been also been demonstrated to react with salivary proteins by thioacetal formation as illustrated in FIG. 1, thereby reducing the negative charge density on the surface of the protein and thus, the protein interaction with the positively charged pyridinium ring of CPC.

When combined, the anionic agent and aldehyde provide even better anti-staining results compared to using these agents separately. It is believed the combination enables stronger interaction between the aldehyde and the protein compared to the interaction between the protein and CPC, as CPC is now tightly bound to a large anionic counter ion and thus less available to interact with the protein. This would explain the observed synergy when using the combination of a lightly charged anionic agent and certain aldehydes or ketones in studies described below.

Similarly we have demonstrated that the use of ethoxylates having the right balance of alkyl and ethoxy units can effectively solubilize salivary proteins, thereby reducing staining. Importantly, the use of the above agents do not significantly impact the bioavailability of CPC, which is surprising and unexpected, given previous findings that the bioavailability of quaternary ammonium antimicrobials is affected by the presence of anionic materials and even nonionic materials that have some partial negative charge (due to hydroxyl, ester, aldehydes and ketone functional groups) as in some ethoxylated surfactants (US20050169852A1 to Roberge, et al.).

A similar approach can be used to control tooth staining derived from other cationic antimicrobials such as stannous, zinc or copper salts used in dentifrice, gel or rinse oral care products.

Evaluation of Tooth Staining Potential of Cationic Antimicrobials and Anti-Staining Activity of Agents:

A. In Vitro Models

Two models were used to evaluate tooth staining potential of compositions containing cationic antimicrobials. CPC was used as the model stain-promoting antimicrobial. The general protocols for the models described below are summarized in FIG. 2.

HAP-Pellicle Model:

The protocol of the HAP-pellicle model involves the development of a pellicle on hydroxyapatite (HAP) powder to simulate pellicle covered teeth. The procedure starts by incubating 10 mg of HAP powder with pooled parotid saliva at 35C for 1 hour. The saliva is removed after centrifugation and the prepared HAP powder is treated with CPC solution (positive control), water (negative control) or CPC test rinse solution for 1 minute in the presence of saliva. Each treatment solution (controls and test) is removed after centrifugation. The HAP residue is washed with saliva for 1 minute and removed after centrifugation. It is then treated with tea solution for 1 minute. The tea solution is then removed from the treated HAP after centrifugation. The treated HAP is washed with saliva as described earlier. 2 additional cycles of treatment are carried out. After 3 cycles of treatment, the HAP is dissolved and absorbance read from 350-550 nm. The AUC (Area Under the Curve) of absorbance between 350-550 nm is the measure of stain. Each test set is run in triplicate.

Bovine Tooth Model

This model utilizes extracted bovine teeth which have been mounted on polyacrylic material. Bovine tooth are first bleached with dilute peroxide followed by washing with water. The bleached teeth are incubated with saliva for 4 hours and then dried. The teeth are then imaged to get baseline color values (L*a*b*), using digital photography using the white light imaging system (Fuji 2000 Camera). The teeth are then incubated in saliva for 18 hours to generate a mature pellicle coating. The saliva is then removed and the teeth are treated with a dentifrice slurry (containing no antimicrobials) for 2 minutes. The dentifrice slurry is removed and the teeth are washed with water for 1 minute. The teeth specimens are now ready for treatment. Teeth specimens are treated with CPC solution (positive control), water (negative control) or CPC test rinse solution for 1 minute in the presence of saliva. The teeth are then incubated with saliva for 20 minutes at 35° C. Each specimen is subsequently treated with a freshly made tea solution for 15 minutes, followed by another washing and incubation with saliva for 20 minutes. A total of 6 treatment cycles are carried out. After 6 cycles, the teeth are dried and L*a*b* values are measured using photo imaging. L* represents lightness on the y axis, a* represents chroma (red-green) on the x axis, and b* represents chroma (yellow-blue) on the z axis. Changes in the individual L*, a*, and b* components ($\Delta$ values) are calculated by subtracting the L*a*b* measurements of treated teeth from the L*a*b* measurements of untreated and unstained teeth. The total color change ($\Delta E$) is calculated as the square root of the sum of the square of the $\Delta$ values. All tests are carried out with a replicate of four teeth.

B. Evaluation of Anti-Staining Activity of Aldehydes, Ketones and Anionic Agents Mouth rinse formulations were evaluated in the bovine tooth model described above. The treatment composition contained 0.07% CPC as antimicrobial and anisaldehyde, anionic chelant or combinations as anti-staining agent. The base composition containing 0.07% CPC without anti-staining agent was the positive (staining) control and water was the negative (non-staining) control. Results are shown below.

| Treatment Group | % Reduction in stain (normalized) |
|---|---|
| 0.07% CPC Base | 0.00 |
| Base + 0.1% Anisaldehyde | 24.20 |
| Base + 0.15% TK Pyrophosphate | 30.08 |
| Base + 0.1% CM Dextran | 31.18 |
| Base + 0.1% Anisaldehyde/0.15% TK Pyro | 95.62 |
| Base + 0.1% Anisaldehyde/0.1% CM Dextran | 81.11 |
| Water | 100.00 |

These results demonstrate that each of the agents used alone provide reduction of stain. Surprisingly, there was synergy on the combination of anisaldehyde with either CM dextran or tetrapotassium pyrophosphate (TKPP) in reducing or nearly eliminating staining. Importantly, the bioavailability of the CPC in the rinse formulations as measured using in vitro Disk Retention Assay (DRA) was between 80-100%, indicating that the anti-stain additives did not significantly affect CPC bioavailability. The DRA method is described in commonly assigned application WO 05/072693 and in S. J. Hunter-Rinderle, et al., "Evaluation of Cetylpyridinium Chloride-Containing Mouthwashes Using In Vitro Disk Retention and Ex Vivo Plaque Glycolysis Methods," *J. Clin. Den.*, 1997, 8:107-113. These assays are recommended for use in the proposed OTC monograph (*Federal Register Vol.* 68, No. 103 Part 356, "Oral Health Care Drug Products For Over-The-Counter Human Use; Antigingivitis/Antiplaque Drug Products; Establishment of a Monograph: Proposed Rules"). This method is designed as a performance assay to analyze mouth rinse formulations containing from about 0.03% to about 0.1% CPC to quantitatively determine the "free" ("unbound") or "bioavailable" level of CPC needed for clinical efficacy. The DRA measures the amount of CPC "binding" to standardized cellulose filter disks during filtration of an undiluted mouth rinse sample. The "bioavailable" CPC binds to the hydroxyl groups on the cellulose fiber during filtration while CPC, which has been rendered "non-bioavailable" (or "bound") through interactions with mouth rinse components, simply passes through the filter paper, i.e., the positive charge on the compound is no longer available for binding to the negatively charged cellulose disks. In this way, the DRA test provides an estimate of the amount of CPC available for activity, i.e., binding to bacteria and mucosal surfaces, during use of the mouth rinse. DRA measurements of CPC availability have been positively correlated to results of in vitro microbiological assays and in vivo germ kill tests. Historically, cellulose fibers have been used in other applications to similarly monitor biological activity of drug actives ("Dairy Products" in Official Methods of Analysis of the Association of Chemical Analytical Chemists. 13$^{th}$ ed., 1980, Chapter 16:256). The method has been validated and shown to perform with acceptable accuracy, precision, and selectivity.

Mouth rinse formulations comprising from about 0.035 to about 0.1% CPC would pass the DRA test if assay results show the level of bioavailable CPC to be $\geq 324$ ppm. For example, a formulation comprising 0.05% CPC at 72% bioavailability would provide 360 ppm CPC. Testing of products containing bioavailable levels of CPC of $\geq 324$ ppm demonstrates positive clinical (antigingivitis, antiplaque) outcomes. Determination of CPC bioavailability in a finished product is important to product performance as it readily defines the amount (concentration) of active available for deposition at the site of action. Because the positively charged (cationic) hydrophilic region is critical to antimicrobial activity, any formulation component that diminishes the activity of this cationic group or that competes with the group may inactivate the product. Desirably, a formulation containing 0.05% CPC would have at least about 65% bioavailability to deliver at least about 324 ppm bioavailable CPC. A formulation containing a lower level of CPC such as 0.04% would need to have at least about 81% bioavailability to deliver the minimum required level of bioavailable CPC for antigingivitis efficacy. Depending upon the particular application and the concentration of CPC or other quaternary ammonium agent, about 50% bioavailability may be acceptable.

Chemical structure activity modeling of stain reduction data (using the HAP saliva pellicle model to evaluate mouth rinses containing 0.07% cetylpyridinium chloride) was carried out. Water was used as the negative control and 0.07% solution of cetylpyridinium chloride was the positive control.

The data set was used to develop a Structural Activity Relationship (SAR) model to correlate the observed reduction of stain to specific chemical structural features of test compounds. The best regression equation was determined and further used to predict % reduction of stain for other chemical ingredients. In order to develop the QSAR (Quantitative Structural Activity Relationship), the % reduction of stain as determined by the above experiment at 0.1% anti-stain active concentration was used in the CaChe 7.1 molecular modeling programme from Fujitsu Limited. The % Reduction of Stain from a training set of 15 chemical samples was used to calculate the Complete Quantum QSAR. The CACHe MOPAC (Molecular Orbital Package) application determines both an optimum geometry and the electronic properties of molecules by solving the Schrödinger equation using the semi-empirical Hamiltonians AM1, PM3 and PM5, developed by M. J. S. Dewar and J. J. P. Stewart. [See *J. Am. Chem. Soc.* (1985), 107, 3902; *J. Comput. Chem.* (1989), 10, 209; MOPAC 2002, (1999).] The following regression equation, which is the best from 50803424 possible triple combinations of 674 descriptors, gave the highest r^2=0.8849.

% Reduction in stain from $CPH = -0.2535*(\text{Carbon count})^2 - 15.9064*\text{sqrt(donatable hydrogen count)} - 956.4721*1.0/[\text{cube root(bonded gravitational index)}] + 130.7168$ The cross-validated correlation coefficient (cvr$^2$=0.7998) suggests that the stability of the equation on addition of similar training data is likely to be reasonable as it is above 0.70. Eq. 1 below calculates the bonded gravitational index ($G_I$) over all bonded atoms i, j in the molecule, which reflects the effective mass distribution in the molecule and effectively describes the molecular dispersion forces in the bulk liquid media.

$$G_I = \Sigma_{ij}^{\text{over all bonded atoms}} (m_i m_j / r_{ij}^2) \qquad \text{Eq. 1}$$

In the above equations, carbon count=total number of carbon atoms in the molecule, donatable hydrogen count=number of hydrogen atoms in a molecule that has labile H atoms (such as in OH, COOH and $NH_2$ groups), $m_i$ and $m_j$=the atomic masses of the bonded atoms, and $r_{ij}$=respective bond lengths.

Based on the above model, the predicted Normalized % Stain Reduction values of many other reactive carbonyl compounds are listed below. These compounds have a predicted stain reduction that is comparable to anisaldehyde. The stain reduction from 0.07% CPC solution (positive control) was normalized with water having stain reduction of 100%, i.e., produced no stain. Preferred among the agents listed below are those having a % normalized stain reduction value of at least about 10%, at least about 20%, at least about 30% or at least about 40%. Agents having below about 10% stain reduction in this model are predicted to have minimal performance.

| Active | Normalized % Stain Reduction |
| --- | --- |
| heliotropin | 82.87 |
| veratraldehyde | 70.35 |
| 3-methyl-1,2-cyclopentadione | 55.33 |
| anisaldehyde | 54.93 |
| phenethyl formate | 54.77 |
| acetophenone | 40.46 |
| phenylacetaldehyde | 40.03 |
| 4-methylacetophenone | 37.07 |
| p-Toluacetaldehyde | 36.65 |
| Isophorone | 33.95 |
| gamma-undecalactone | 31.87 |
| p-methyl cinnamaldehyde | 30.58 |
| benzylacetone | 29.55 |
| octanal | 28.84 |
| (−) piperitone | 28.70 |
| perillaldehyde | 27.58 |
| cuminaldehyde | 26.80 |
| α-methyl cinnamaldehyde | 26.49 |
| isomenthone | 26.03 |
| menthone | 26.00 |
| carvone | 23.64 |
| decanal | 20.78 |
| maltol | 20.24 |
| p-Isopropylphenylacetaldehyde | 19.37 |
| trans-citral | 17.81 |
| dihydrojasmone | 17.56 |
| beta-napthylmethyl ketone | 13.15 |
| tiglic aldehyde | 8.85 |
| ethyl vanillin | 7.03 |
| isovaleraldehyde | 6.39 |

Using chemical structure activity modeling described above and the Bovine tooth Model, the following anionic compounds are anticipated to have similar anti-staining activity as carboxymethyl dextran and tetrapotassium pyrophosphosphate. These compounds contain anionic phosphate, carboxy or sulfate groups, are at least slightly water soluble or water-dispersible and are used in the acid form or as alkali metal or ammonium salts thereof. Preferred anionic agents are those having a % normalized stain reduction value of at least about 10%, at least about 20%, at least about 30% or at least about 40%.

| Active | Normalized % stain reduction |
| --- | --- |
| tetra potassium pyrophosphate | 55.15 |
| phytic acid | 42.99 |
| D-fructose-1-6-biphosphate | 41.83 |
| dihydroxyacetone phosphate | 40.70 |
| D-Erythrose-4-phosphate | 34.40 |
| Glycerol phosphate | 33.43 |
| creatine phosphate | 30.70 |
| D-ribose-5-phosphate | 28.31 |
| D-fructose-6-phosphate | 28.16 |
| D-xylose-5-phosphate | 24.73 |
| glyceraldehyde-3-phosphate | 22.66 |
| α-D-glueose-6-phosphate | 15.65 |
| α-D-glueose-1-phosphate | 15.52 |
| uridine-5-phosphate | 11.37 |
| ascorbyl phosphate | 11.35 |
| Xylitol-5-phosphate | 8.01 |
| DL malic acid | 6.61 |

The following polymeric materials are anticipated to have anti-staining activity: dextran sulfate; lower molecular weight polymers (about 15,000 or less) such as carboxymethyl hydroxypropylcellulose, carboxymethyl methylcellulose; acrylic-maleic acid copolymers; and carboxymethyl starch. Polymers having a low charge density are preferred. Examples include lightly charged carboxylated, phosphated or sulfated water soluble polymers such as celluloses, dextrans, starches and the like with a degree of anionic group substitution (DS) of 0.2 or less. DS of 0.2 is defined as 2 anionic group substituent units (e.g., carboxymethyl, phosphate or sulfate) per 10 repeating units in the polymer, e.g., glucose units in cellulose). By "water soluble polymers" herein is meant to include polymers that are solvatable or hydratable with water forming transparent, translucent, or semi-opaque solutions or gels, which are generally accepted as uniformly dispersed in water or in a predominately water containing medium. It is known that water soluble polymers do not necessarily form "true" solutions but can exist as hydrated particles that are fully or partially solvated and uncoiled.

A lower molecular weight of the polymer is preferred as lower viscosity build in the formulation may be desired. For example, for a mouth rinse formulation the desired viscosity is about 1 to 5 cP. Furthermore, it is believed that the lower molecular weight polymers can better interact with the salivary proteins and partition into one another better. At higher molecular weights (>15,000), the protein would interact with an entangled polymer network rather than identifiable polymer strands or coils and the protein partition coefficient would become independent of molecular weight. The anionic polymers useful herein would have average molecular weight (MW) of about 15,000 or less, about 10,000 or less or about 5000 or less.

C. Evaluation of Anti-Staining Activity of Nonionic Ethoxylated Surfactants (Ethoxylates)

The staining potential of an emulsion rinse containing 0.1% CPC and 0.3% flavor oil was evaluated using 0.05% of a nonionic ethoxylated linear alcohol surfactant (available under the tradename Performathox 490 from Baker Hughes, MW=4522; HLB 18), having the following general structure. Staining results as evaluated by the bovine tooth model are as follows.

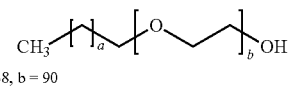

a = 38, b = 90

| Group | Group delta E | % Stain Reduction |
| --- | --- | --- |
| 0.07% CPC | 19.02 | 0.0 |
| 0.07% CPC + 0.05% | 15.92 | 43.7 |

-continued

| Group | Group delta E | % Stain Reduction |
|---|---|---|
| Performathox 490 Water | 11.94 | 100.0 |

The HAP-pellicle model was used to evaluate ethoxylates of different carbon chain lengths, EO units, EO weight %, HLB and molecular weights for stain reduction when incorporated at different concentrations in an emulsion rinse containing 0.1% CPC as described in co-filed patent application entitled MOUTH RINSE EMULSIONS. Results are summarized in Table 1 below. A positive # for Normalized Stain Reduction from base rinse indicates a reduction in stain while a negative number indicates increased staining. Modeling of the resultant data set indicates that ethoxylated alcohols having 18 or more carbons in the alcohol chain, about 35 or more EO (ethylene oxide) units and molecular weight between about 2,000 to about 15,000 would provide a benefit in stain reduction without compromising bioavailability of CPC. Preferred for use herein are ethoxylates having about 25 to 55 carbons in the alcohol chain, from 50 to 100 EO units and MW between about 2,000 to about 5,000.

TABLE 1

Evaluation of Anti-Stain Performance of Ethoxylates

| Material | # Carbons (tail) | # EO Units | % EO by Wt. | HLB | Mol. Wt. | % Polymer | Normalized Stain Reduction | DRA |
|---|---|---|---|---|---|---|---|---|
| Sigma 458988 | 34 | 10 | 50 | 10 | 920 | 0.05 | −64.61 | 95.09 |
| Sigma 458988 | 34 | 10 | 50 | 10 | 920 | 0.1 | −85.81 | 93.98 |
| Sigma 458988 | 34 | 10 | 50 | 10 | 920 | 0.2 | −95.58 | 91.71 |
| Brij 30 (Brij L4) | 12 | 4 | 51 | 9.7 | 362 | 0.05 | −42.95 | 90.99 |
| Brij 30 (Brij L4) | 12 | 4 | 51 | 9.7 | 362 | 0.1 | −64.30 | 80.98 |
| Brij 30 (Brij L4) | 12 | 4 | 51 | 9.7 | 362 | 0.2 | −88.15 | 71.78 |
| Brij 98 (Brij O 20) | 18 | 20 | 78 | 18 | 1150 | 0.05 | −18.95 | 86.95 |
| Brij 98 (Brij O 20) | 18 | 20 | 78 | 18 | 1150 | 0.1 | 12.25 | 71.79 |
| Brij 98 (Brij O 20) | 18 | 20 | 78 | 18 | 1150 | 0.2 | 46.61 | 62.87 |
| Performathox 450 | 34 | 10 | 50 | 10 | 920 | 0.05 | −23.37 | 91.5 |
| Performathox 450 | 34 | 10 | 50 | 10 | 920 | 0.1 | −33.73 | 84.3 |
| Performathox 450 | 34 | 10 | 50 | 10 | 920 | 0.15 | −37.57 | 81.4 |
| Performathox 450 | 34 | 10 | 50 | 10 | 920 | 0.2 | −45.31 | 75.5 |
| Performathox 480 | 34 | 40 | 80 | 16 | 2300 | 0.05 | 6.39 | 90.1 |
| Performathox 480 | 34 | 40 | 80 | 16 | 2300 | 0.1 | 19.09 | 82.1 |
| Performathox 480 | 34 | 40 | 80 | 16 | 2300 | 0.15 | 33.96 | 74.8 |
| Performathox 480 | 34 | 40 | 80 | 16 | 2300 | 0.2 | 26.02 | 71.8 |
| Performathox 490 | 40 | 90 | 90 | 18 | 4522 | 0.05 | 13.68 | 86.2 |
| Performathox 490 | 40 | 90 | 90 | 18 | 4522 | 0.1 | 18.77 | 80.9 |
| Performathox 490 | 40 | 90 | 90 | 18 | 4522 | 0.15 | 43.37 | 75.9 |
| Performathox 490 | 40 | 90 | 90 | 18 | 4522 | 0.2 | 32.71 | 72.6 |
| Performathox 750 | 50 | 16 | 50 | 10 | 1400 | 0.05 | −51.84 | 96.3 |
| Performathox 750 | 50 | 16 | 50 | 10 | 1400 | 0.1 | −41.43 | 93.4 |
| Performathox 750 | 50 | 16 | 50 | 10 | 1400 | 0.15 | −72.63 | 92.2 |
| Performathox 750 | 50 | 16 | 50 | 10 | 1400 | 0.2 | −92.81 | 88.6 |
| Brij S100 | 18 | 100 | 94 | 18.8 | 4654 | 0.05 | 19.82 | 85.5 |
| Brij S100 | 18 | 100 | 94 | 18.8 | 4654 | 0.1 | 19.82 | 78.7 |
| Brij S100 | 18 | 100 | 94 | 18.8 | 4654 | 0.15 | 26.57 | 74.4 |
| Brij S100 | 18 | 100 | 94 | 18.8 | 4654 | 0.2 | 34.76 | 71.7 |

The total amount of anti-stain agent included in the present compositions will be from about 0.01% to about 5%, from about 0.025% to about 3% or from about 0.1% to about 2%. The anti-stain agents will be at least slightly water-soluble (about 0.1% solubility at 25° C., preferably higher) or be water-dispersible for optimum interaction with salivary proteins and the cationic antimicrobial agent.

Cationic Antimicrobial Agents

Cationic antimicrobial agents that are known for their propensity to induce tooth staining include quaternary ammonium salts, bis-biquanide salts; and metal ion sources that provide metal ions such as stannous, zinc and copper. These cationic agents provide effectiveness in killing, and/or altering metabolism, and/or suppressing the growth of, microorganisms which cause topically-treatable infections and diseases of the oral cavity, such as plaque, caries, gingivitis, and periodontal disease. The level of antimicrobial agent is dependent on the type of antimicrobial agent and other factors and typically will be from about 0.01% to about 5.0%, by weight of the composition.

The quaternary ammonium compounds in the compositions of the present invention include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Cetylpyridinium chloride, cetyl pyridinium fluoride, tetradecylpyridinium chloride, N-tetradecyl-4-ethyl pyridinium chloride, domiphen bromide, benzalkonium chloride, benzethonium chloride, methyl benzethonium chloride, dodecyl trimethyl ammonium bromide, dodecyl dimethyl (2-phenoxyethyl) ammonium bromide, benzyl dimethoxystearyl ammonium chloride, quaternized 5-amino-1,3-bis (2-ethyl-hexyl)-5-methyl hexa hydropyrimidine, lauryl trimethylammonium chloride, cocoalkyl trimethylammonium chloride, cetyl trimethylammonium bromide, di-isobutyl-phenoxyethyl-dimethylbenzylammonium chloride, dodecyl trimethyl ammonium bromide, are exemplary of typical quaternary ammonium antimicrobial agents. Other compounds are bis[4-(R-amino)-1-pyridinium] alkanes as disclosed in U.S. Pat. No. 4,206,215 to Bailey. The pyridinium compounds are the preferred quaternary ammonium compounds, particularly preferred being cetylpyridinium, or tetradecylpyridinium halide salts (i.e., chloride, bromide, fluoride and iodide). Particularly preferred are cetylpyridinium chloride and fluoride salts. The quaternary ammonium antimicrobial agents are included in the present invention at levels of at least about 0.025 or at least about 0.035% or at least about 0.045% to about 1.0%, or from about 0.025% to about 0.1% by weight of the composition.

The present compositions may comprise a metal ion source that provides stannous ions, zinc ions, copper ions, or mixtures thereof as antimicrobial agent. The metal ion source can be a soluble or a sparingly soluble compound of stannous, zinc, or copper with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous, zinc, and copper.

Stannous, zinc and copper ions have been found to help in the reduction of gingivitis, plaque, sensitivity, and improved breath benefits. The composition may comprise from about 50 ppm to about 20,000 ppm metal ion of the total composition, from about 500 ppm to about 15,000 ppm or from about 3,000 ppm to about 10,000 ppm. This is the total amount of metal ions (stannous, zinc, copper and mixtures thereof) for delivery to the tooth surface.

Dentifrices containing stannous salts, such as stannous fluoride and stannous chloride, are described in U.S. Pat. No. 5,004,597 to Majeti et al. Other descriptions of stannous salts and ingredients needed to stabilize the stannous are found in U.S. Pat. No. 5,578,293 issued to Prencipe et al. and in U.S. Pat. No. 5,281,410 issued to Lukacovic et al.

Stannous salts useful herein include stannous fluoride and stannous chloride dihydrate, stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880. Examples of suitable copper ion sources are listed in U.S. Pat. No. 5,534,243 and include the chloride, sulfate gluconate, and glycinate salts. The combined metal ion sources will typically be present in an amount of from about 0.05% to about 11%, by weight of the final composition, from about 0.5 to about 7%, or from about 1% to about 5%. The stannous salts will typically be present in an amount of from about 0.1 to about 7%, from about 1% to about 5%, or from about 1.5% to about 3% by weight of the total composition. The amount of zinc or copper salts will typically range from about 0.01 to about 5%, from about 0.05 to about 4%, or from about 0.1 to about 3.0%. Preferred metal ion sources include stannous fluoride, stannous chloride, stannous chloride dihydrate, zinc citrate, zinc lactate, zinc sulfate, zinc chloride, zinc acetate, zinc oxide, copper sulfate, and copper gluconate.

Additional Antimicrobial Agents

The present compositions may additionally comprise other orally-effective antimicrobial agents including non-cationic agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, essential oils; enzymes such as endoglycosidase, papain, dextranase, mutanase, and mixtures thereof. The level of other antimicrobial agent will also depend on the type of antimicrobial agent and other factors and typically will be from about 0.01% to about 5.0%, by weight of the composition.

Antimicrobially-effective essential oils include one or more of flavor/fragrance chemicals such as citral, neral, geranial, geraniol, nerol, eucalyptol, eugenol, eugenyl acetate, carvacrol, thymol, o-cymen-5-ol (isopropylmethylphenol, IPMP), farnesol, benzyl alcohol, benzaldehyde, hinokitiol (isopropyltropolone), terpinene-4-ol, zingerone, allyl isothiocyanate, dipentene, α-pinene, β-pinene, menthol, methyl salicylate, anethole, carvone, limonene, ocimene, n-decyl alcohol, citronellal, citronellol, methyl acetate, citronellyl acetate, methyl eugenol, linalool, ethyl linalool, camphor, safrole, chlorothymol, guaiacol, phenol, phenyl salicylate, cinnamic acid, guaiacol, isoeugenol, dihydroeugenol, vanillyl butyl ether, 5-propenylguaethol, 4-ethyl-2-methoxyphenol, 4-allyl-2-methoxyphenol acetate, and 4-methyl guaiacol. Natural sources of these chemicals may be used. The selection of the essential oils to is based on demonstration of their activity against microorganisms known to be involved in undesirable oral cavity conditions such as gingivitis, periodontal disease and oral malodor. For example, useful herein is a blend of essential oils comprising at least two components, a first component selected from acyclic or non-ring structures such as citral, neral, geranial, geraniol, nerol or derivatives thereof and a second component selected from ring-containing structures such as eucalyptol, eugenol, carvacrol or derivatives thereof. These essential oil blends are described in commonly-assigned patent application published as US20080253976A1. The essential oil blend is used at a level of at least about 0.02% by weight of the composition to provide effective antimicrobial activity.

A number of the above antimicrobially effective essential oil chemicals are aldehydes and ketones which are useful as anti-stain agents.

In addition to the components described above, the present compositions may comprise additional optional components collectively referred to as orally acceptable carrier materials, which are described in the following paragraphs.

Orally Acceptable Carrier Materials

The orally acceptable carrier materials comprise one or more compatible solid or liquid excipients or diluents which are suitable for topical oral administration. By "compatible," as used herein, is meant that the components of the composition are capable of being commingled without interaction in a manner which would substantially reduce the composition's stability and/or efficacy. In particular, the carrier materials should not have a negative effect on the bioavailability of the cationic antimicrobials or on the anti-staining activity of the anti-stain agents used herein.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433 to Benedict. Carrier materials for biphasic dentifrice formulations are disclosed in U.S. Pat. No. 5,213,790, issued May 23, 1993, U.S. Pat. Nos. 5,145,666, and 5,281,410 all to Lukacovic et al. and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955 to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani. Carriers suitable for the preparation of compositions of the present invention are well known in the art. Their selection will depend on secondary considerations like taste, cost, and shelf stability, etc.

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, said implement being impregnated with the present composition. The dental implement can be impregnated fibers including dental floss or tape, chips, strips, films and polymer fibers.

In one embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other embodiments of the subject invention are liquid products, including mouthwashes or mouth rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Types of orally acceptable carrier materials or excipients, which may optionally be included in compositions of the present invention, along with specific non-limiting examples, are described in the following paragraphs.

Desensitizing Agent

The present compositions may optionally contain a dentinal desensitizing agent such as salts of potassium, calcium, strontium and tin including nitrate, chloride, fluoride, phosphates, pyrophosphate, polyphosphate, citrate, oxalate and sulfate.

Anticalculus Agent

The present compositions may optionally include an anticalculus agent, such as a pyrophosphate salt as a source of pyrophosphate ion. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, or less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, from about 2% to about 10%, or from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology*, Third Edition, Volume 17, Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977, to Gaffar et al., as well as, e.g., polyamino propane sulfonic acid (AMPS), diphosphonates (e.g., EHDP; AHP), polypeptides (such as polyaspartic and polyglutamic acids), and mixtures thereof.

Fluoride Ion Source

It is common to have a water-soluble fluoride compound present in dentifrices and other oral compositions in an amount sufficient to give a fluoride ion concentration in the composition, and/or when it is used of from about 0.0025% to about 5.0% by weight or from about 0.005% to about 2.0% by weight, to provide anticaries effectiveness. A wide variety of fluoride ion-yielding materials can be employed as sources of soluble fluoride in the present compositions.

Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al. Representative fluoride ion sources include: stannous fluoride, sodium fluoride, potassium fluoride, sodium monofluorophosphate, indium fluoride, amine fluoride and many others. Stannous fluoride and sodium fluoride are among preferred sources, as well as mixtures thereof.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley and Grabenstetter. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230 and DiGiulio, U.S. Pat. No. 3,862,307. Examples include the silica xerogels marketed under the trade name "Syloid" by the W.R. Grace & Company, Davison Chemical Division and precipitated silica materials such as those marketed by the J. M. Huber Corporation under the trade name, Zeodent®, particularly the silicas carrying the designation Zeodent® 119, Zeodent® 118, Zeodent® 109 and Zeodent® 129. The types of silica dental abrasives useful in the toothpastes of the present invention are described in more detail in Wason, U.S. Pat. No. 4,340,583; and in commonly-assigned U.S. Pat. Nos. 5,603,920; 5,589,160; 5,658,553; 5,651,958; and 6,740,311.

Mixtures of abrasives can be used such as mixtures of the various grades of Zeodent® silica abrasives listed above. The total amount of abrasive in dentifrice compositions of the subject invention typically range from about 6% to about 70% by weight; toothpastes generally contain from about 10% to about 50% of abrasives, by weight of the composition. Dental solution, mouth spray, mouthwash and non-abrasive gel compositions of the subject invention typically contain little or no abrasive.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals or teeth.

PMSA's are useful in the present compositions because of their stain prevention benefit. The PMSA's may provide a stain prevention benefit because of their reactivity or substantivity to mineral surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products, for example, stannous ions and cationic antimicrobials, is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these polymeric agents are also known or expected to provide tartar control benefits when applied in oral compositions, hence providing improvement in both the appearance of teeth and their tactile impression to consumers.

The polymeric mineral surface active agents include an agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977, to Gaffar et al. Diphosphonate modified polyacrylic acid is another example. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers). Suitable polymers include the diphosphonate/acrylate polymers supplied by Rhodia under the designation ITC 1087 (Average MW 3000-60,000) and Polymer 1154 (Average MW 6000-55,000).

Suitable PMSA's will be stable and compatible with other components of the oral care composition such as ionic fluoride, cationic antimicrobials and metal ions, and are stable to hydrolysis in high water content formulations, thus permitting a simple single phase dentifrice or mouth rinse formulation. If the PMSA does not have these stability and compatibility properties, one option is a dual phase formulation with the PMSA separated from the fluoride or other incompatible component. Another option is to formulate non-aqueous, essentially non-aqueous or limited water compositions to minimize reaction between the PMSA and other components.

A preferred PMSA is a polyphosphate. A polyphosphate is generally understood to consist of two or more phosphate molecules arranged primarily in a linear configuration, although some cyclic derivatives may be present. Preferred polyphosphates are those having around three or more phosphate groups so that surface adsorption at effective concentrations produces sufficient non-bound phosphate functions, which enhance the anionic surface charge as well as hydrophilic character of the surfaces. The polyphosphate salts desired include tripolyphosphate, tetrapolyphosphate and hexametaphosphate, among others. Polyphosphates larger than tetrapolyphosphate usually occur as amorphous glassy materials. Preferred in this invention are the linear polyphosphates having the formula: $XO(XPO_3)_nX$, wherein X is sodium, potassium or ammonium and n averages from about 3 to about 125. Preferred polyphosphates are those having n averaging from about 6 to about 21, such as those commercially known as Sodaphos (n≈6), Hexaphos (n≈13), and Glass H (n≈21) and manufactured by FMC Corporation and Astaris. These polyphosphates may be used alone or in combination. Some polyphosphates are susceptible to hydrolysis in high water formulations at acid pH, particularly below pH 5. Thus it is preferred to use longer-chain polyphosphates, such as Glass H having an average chain length of about 21. Such longer-chain polyphosphates when undergoing hydrolysis, produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

The amount of tooth substantive agent may be from about 0.1% to about 35% by weight of the total oral composition. In dentifrice formulations, the amount is typically from about 2% to about 30%, from about 5% to about 25%, or from about 6% to about 20%. In mouth rinse compositions, the amount of tooth substantive agent is typically from about 0.1% to 5% or from about 0.5% to about 3%.

In addition to creating surface modifying effects, the tooth substantive agent may also function to solubilize insoluble salts. For example, Glass H has been found to solubilize insoluble stannous salts. Thus, in compositions containing stannous fluoride for example, Glass H contributes to decreasing the stain promoting effect of stannous.

Chelating Agents

Another optional agent is a chelating agent, also called sequestrants, such as gluconic acid, tartaric acid, citric acid and pharmaceutically-acceptable salts thereof. Chelating agents are able to complex calcium found in the cell walls of the bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Examples of suitable chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; sodium, potassium or ammonium polyphosphates and mixtures thereof. The amounts of chelating agent suitable for use in the present invention will typically be from about 0.1% to about 2.5%, from about 0.5% to about 2.5%, or from about 1.0% to about 2.5%.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. Nos. 4,138,477 and 4,183,914 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976. The present composition typically comprises an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5% or from about 0.5% to about 2.0% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; cocoalkyl trimethylammonium chloride; cetyl pyridinium fluoride; etc. The quaternary ammonium fluorides having detergent properties are described in U.S. Pat. No. 3,535,421 to Briner et al. Certain cationic surfactants can also act as germicides in the compositions disclosed herein.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic synthetic surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Suitable betaine surfactants are disclosed in U.S. Pat. No. 5,180,577 to Polefka et al. Typical alkyl dimethyl betaines include decyl betaine or 2-(N-decyl-N,N-dimethylammonio) acetate, coco betaine, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice include cocoamidopropyl betaines such as lauramidopropyl betaine.

Thickening Agents

In preparing toothpaste or gels, thickening agents are added to provide a desirable consistency to the composition, to provide desirable active release characteristics upon use, to provide shelf stability, and to provide stability of the composition, etc. Suitable thickening agents include one or a combination of carboxyvinyl polymers, carrageenan, hydroxyethyl cellulose (HEC), natural and synthetic clays (e.g., Veegum and laponite) and water soluble salts of cellulose ethers such as sodium carboxymethylcellulose (CMC) and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Suitable carboxyvinyl polymers useful as thickening or gelling agents include carbomers which are homopolymers of acrylic acid crosslinked with an alkyl ether of pentaerythritol or an alkyl ether of sucrose. Carbomers are commercially available from B.F. Goodrich as the Carbopol® series, including Carbopol 934, 940, 941, 956, and mixtures thereof.

Thickening agents are typically present in an amount from about 0.1% to about 15%, from about 2% to about 10%, or from about 4% to about 8%, by weight of the total toothpaste or gel composition, can be used. Higher concentrations may be used for chewing gums, lozenges and breath mints, sachets, non-abrasive gels and subgingival gels.

Humectants

Another optional carrier material of the present compositions is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70% or from about 5% to about 25%, by weight of the compositions herein. Suitable humectants for use in compositions of the subject invention include edible polyhydric alcohols such as glycerin, sorbitol, xylitol, butylene glycol, polyethylene glycol, propylene glycol and trimethyl glycine.

Flavor System

A flavor system is typically added to oral care compositions, to provide a pleasant tasting composition and to effectively mask any unpleasant taste and sensations due to certain components of the composition such as antimicrobial actives or peroxide. Pleasant tasting compositions improve user compliance to prescribed or recommended use of oral care products. The present flavor system will comprise flavor components, such as those that have been found to be relatively stable in the presence of usual oral care product actives, carrier materials or excipients. The flavor system may comprise flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3(2H)-furanone, 5-ethyl-3-hydroxy-4-methyl-2(5H)-furanone, vanillin, ethyl vanillin, 2-methoxybenzaldehyde, benzaldehyde; cinnamaldehyde, hexyl cinnamaldehyde, α-methyl cinnamaldehyde, ortho-methoxy cinnamaldehyde, α-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, maltol, ethyl maltol, anethole, dihydroanethole, carvone, menthone, β-damascenone, ionone, gamma-decalactone, gamma-nonalactone, gamma-undecalactone and mixtures thereof. Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents are generally used in the compositions at levels of from about 0.001% to about 5%, by weight of the composition.

The flavor system will typically include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under as sucralose as well as protein based sweeteners such as thaumatoccous danielli (Thaumatin I and II) can be used. A composition typically contains from about 0.1% to about 10% of sweetener, by weight.

Suitable cooling agents or coolants include a wide variety of materials such as menthol and derivatives thereof. Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-p-menthan-3-carboxamide, known commercially as "WS-3", and others in the series such as WS-5, WS-11, WS-14 and WS-30. An example of a synthetic carboxamide coolant that is structurally unrelated to menthol is N,2,3-trimethyl-2-isopropylbutanamide, known as "WS-23". Additional suitable coolants include 3-1-menthoxypropane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. The terms menthol and menthyl as used herein include dextro- and levorotatory isomers of these compounds and racemic mixtures thereof. TK-10 is described in U.S. Pat. No. 4,459,425, Amano et al. WS-3 and other carboxamide cooling agents are described for example in U.S. Pat. Nos. 4,136,163; 4,150,052; 4,153,679; 4,157,384; 4,178,459 and 4,230,688. Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)-ρ-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide.

In addition the flavor system may include sensates such as salivating agents, hydration and moisturization agents, warming agents, and numbing agents. These agents are present in the compositions at a level of from about 0.001% to about 10% or from about 0.1% to about 1%, by weight of the composition. Suitable salivating agents include Jambu® manufactured by Takasago and Optaflow® from Symrise. Examples of hydration agents include polyols such as erythritol. Suitable numbing agents include benzocaine, lidocaine, clove bud oil, and ethanol. Examples of warming agents include ethanol, capsicum and nicotinate esters, such as benzyl nicotinate.

Miscellaneous Carrier Materials

Water employed in the preparation of commercially suitable oral compositions desirably would be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including effervescent, abrasive, deodorant, buffering and adjusting pH. The present composition may contain from about 0.5% to about 30%, from about 0.5% to about 15% or from about 0.5% to about 5% of an alkali metal bicarbonate such as sodium bicarbonate.

The pH of the present compositions may be adjusted through the use of buffering agents. Buffering agents, as used herein, refer to agents that can be used to adjust the pH of aqueous compositions such as mouth rinses and dental solutions typically to a range of about 3 to about 8, preferably from about 3 to about 6. Buffering agents include sodium bicarbonate, monosodium phosphate, trisodium phosphate, sodium hydroxide, sodium carbonate, sodium acid pyrophosphate, citric acid, and sodium citrate. Buffering agents are typically included at a level of from about 0.5% to about 10%, by weight of the present compositions.

Emulsifying agents may be employed in the present compositions. Examples of emulsifying agents include poloxamers described above as a nonionic surfactant, which may also function as binder, stabilizer, and other related functions. Poloxamers are difunctional block-polymers terminating in primary hydroxyl groups with molecular weights ranging from 1,000 to above 15,000. Poloxamers are sold under the tradename of Pluronics and Pluraflo by BASF, such as Poloxamer 407 and Pluraflo L4370. Other suitable emulsifying agents include the polyacrylic acid Pemulen® series available from B.F. Goodrich; Vitamin E acetate; Vitamin E succinate and pegylated Vitamin E.

Titanium dioxide may also be added to the present composition to add opacity to the compositions, typically at from about 0.25% to about 5% by weight of dentifrice compositions.

Other optional agents that may be used in the present compositions include dimethicone copolyols selected from alkyl- and alkoxy-dimethicone copolyols, such as C12 to C20 alkyl dimethicone copolyols and mixtures thereof. An example is cetyl dimethicone copolyol marketed under the trade name Abil EM90. The dimethicone copolyols aid in providing positive tooth feel benefits and may be present at a level of from about 0.01% to about 25%.

Method of Use

The present invention also relates to the use of the compositions for control of staining and for controlling bacterial activity in the oral cavity which cause undesirable conditions including plaque, caries, calculus, gingivitis, and periodontal disease. The benefits of these compositions may increase over time when the composition is used repeatedly.

The method of use or treatment herein comprises contacting a subject's dental enamel surfaces and mucosa in the mouth with the oral compositions according to the present invention. The method may comprise brushing with a dentifrice or rinsing with a dentifrice slurry or mouth rinse. Other methods include contacting the topical oral gel, denture product, mouthspray, or other form with the subject's teeth and oral mucosa. The subject may be any person or animal in need of oral care. By animal is meant to include household pets or other domestic animals, or animals kept in captivity.

For example, a method of treatment may include a person brushing a dog's teeth with one of the dentifrice compositions. Another example would include rinsing a cat's mouth with an oral composition for a sufficient amount of time to see a benefit. Pet care products such as chews and toys may be formulated to contain the present oral compositions. The composition may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

EXAMPLES

The following examples further describe and demonstrate embodiments within the scope of the present invention. These examples are given solely for the purpose of illustration and are not to be construed as limitations of the present invention.

Example I Mouth Rinse Compositions

Mouth rinse compositions A-F according to the present invention made using conventional methods are shown below with amounts of components in weight %.

| Components | A | B | C | D | E | F |
|---|---|---|---|---|---|---|
| Water | QS | QS | QS | QS | QS | QS |
| Glycerin | 5 | 5 | 5 | 5 | 7.5 | 10 |
| Propylene glycol | — | — | — | 3 | — | — |
| Ethanol | — | — | — | — | 3 | 10 |
| Methyl Paraben | — | 0.02 | 0.02 | — | — | — |
| Propyl Paraben | — | 0.005 | 0.005 | — | — | — |
| CPC | 0.074 | 0.074 | 0.074 | 0.05 | 0.07 | 0.1 |
| Sucralose | 0.03 | 0.03 | 0.03 | 0.05 | 0.05 | 0.07 |
| Anisaldehyde | — | 0.1 | 0.1 | 0.1 | — | — |
| CM Dextran | 0.1 | 0.1 | 0.1 | — | 0.05 | 0.1 |
| Flavor/sensate oils | 0.1 | 0.05 | 0.05 | 0.3 | 0.3 | 0.4 |
| Performathox 490 | 0.075 | — | 0.05 | 0.1 | 0.05 | 0.05 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the scope of the invention. The scope of the claims should not be limited by the embodiments set forth in the examples, but should be given the broadest interpretation consistent with the description as a whole.

What is claimed is:

1. An antimicrobial oral care mouth rinse composition effective against dental plaque, calculus, gingivitis and periodontal disease comprising
    (a) cetylpyridinium chloride,
    (b) an anti-stain agent comprising one or more materials from each of at least two of the following chemical groups:
        (i) Group 1 anti-stain agents have a molecular weight of 15,000 or less and are selected from carboxymethyl dextran or tetrapotassium pyrophosphate;
        (ii) Group 2 anti-stain agent anisaldehyde and
        (iii) Group 3 anti-stain agents selected from nonionic ethoxylated linear alcohols, having about 25 to 55 carbons in the alcohol chain, about 50 to about 100 ethoxy units and an average molecular weight of about 2,000 to about 5,000, and (c) a pharmaceutically acceptable carrier, wherein the anti-stain agent is present in an amount effective to inhibit dental stain formation caused by the cationic antimicrobial agent;

wherein the cetylpyridinium chloride has a bioavailability of at least about 50% as measured using an in vitro Disk Retention Assay (DRA); and wherein the composition has a normalized stain reduction value of at least about 40%.

2. An oral care composition according to claim 1, comprising from about 0.01% to about 5% by weight of the composition of the anti-stain agent.

3. An oral care mouth rinse composition comprising
   (a) from about 0.025% to about 0.1% by weight of the composition of cetylpyridinium chloride,
   (b) from about 0.025% to about 3% by weight of an anti-stain agent comprising one or more materials from each of at least two of the following chemical groups:
      (i) Group 1 anti-stain agents having a molecular weight of about 15,000 or less and selected from a carboxymethyl dextran or dextran sulfate,
      (ii) Group 2 anti-stain agent 4-methoxybenzaldehyde (anisaldehyde); and
      (iii) Group 3 anti-stain agents selected from ethoxylated alcohols having from about 25 to 55 carbons in the alcohol chain, about 50 to 100 ethylene oxide units and average molecular weight from about 2,000 to about 5,000, and
   (c) an orally-acceptable carrier comprising one or more materials selected from from a fluoride ion source, additional antimicrobial agent, an anti-inflammatory agent, an anticalculus agent, a desensitizing agent, a peroxide source, a tooth substantive agent, a surfactant, an emulsifying agent, an anti-stain agent, essential oils, a coolant, a sweetening agent or other sensates;
   wherein the cetylpyridinium chloride has a bioavailability of at least about 50% as measured using an in vitro Disk Retention Assay (DRA); and
   wherein the composition has a normalized stain reduction value of at least about 40%.

4. An oral care mouth rinse composition according to claim 3, having a pH ranging from about 3 to about 6.

5. An antimicrobial oral care mouth rinse composition effective against dental plaque, calculus, gingivitis and periodontal disease comprising
   (a) cetylpyridinium chloride,
   (b) an anti-stain agent comprising one or more materials from each of the following chemical groups:
      (i) Group 1 anti-stain agents have a molecular weight of 15,000 or less and are selected from D-fructose-1-6-biphosphate; D-ribose-5-phosphate; dihydroxyacetone phosphate; D-erythrose-4-phosphate; glycerol phosphate; creatine phosphate; D-ribose-5-phosphate; D-fructose-6-phosphate; D-xylose-5-phosphate; glyceraldehyde-3-phosphate; α-D-glucose-6-phosphate; α-D-glucose-1-phosphate; uridine-5-phosphate; or ascorbyl phosphate;
      (ii) Group 2 anti-stain agents selected from aldehydes, ketones or other reactive carbonyl compounds and
      (iii) Group 3 anti-stain agents selected from nonionic ethoxylated linear alcohols, having about 25 to 55 carbons in the alcohol chain, about 50 to about 100 ethoxy units and an average molecular weight of about 2,000 to about 5,000, and
   (c) a pharmaceutically acceptable carrier,
   wherein the anti-stain agent is present in an amount effective to inhibit dental stain formation caused by the cationic antimicrobial agent;
   wherein the cetylpyridinium chloride has a bioavailability of at least about 50% as measured using an in vitro Disk Retention Assay (DRA).

6. An oral care composition according to claim 5, comprising from about 0.01% to about 5% by weight of the composition of the anti-stain agent.

7. An oral care composition according to claim 5, wherein the Group 2 anti-stain agents are selected from 4-methoxybenzaldehyde (anisaldehyde); 1,3-benzodioxole-5-carbaldehyde (heliotropin); 3,4-dimethoxybenzaldehyde (veratraldehyde); 3-methyl-1,2-cyclopentadione; phenethyl formate; acetophenone; phenylacetaldehyde; 4-methylacetophenone; ρ-toluacetaldehyde ; 3, 5, 5-trimethyl-2-cyclohexene-1-one (isophorone); gamma-undecalactone; ρ-methyl cinnamaldehyde; 4-phenyl-2-butanone (benzyl acetone); octanal; 6-isopropyl-3-methyl-1cyclohex-2-enone (piperitone); (S)-4-(1-methylethenyl)-1-cyclohexene-1-carboxaldehyde (perillaldehyde); 4-(1-methylethyl) benzaldehyde (cuminaldehyde); α-methyl cinnamaldehyde; isomenthone; menthone; carvone; decanal; 3-hydroxy-2-methyl-4H-pyran-4-one (maltol); ρ-isopropyl phenylacetaldehyde; trans-citral; 3-methyl-2-pentylcyclopent-2-ene-1-one (dihydrojasmone); or β-napthylmethyl ketone.

8. An oral care mouth rinse composition according to claim 5, having a pH ranging from about 3 to about 6.

* * * * *